(12) United States Patent
Knox et al.

(10) Patent No.: US 9,002,065 B2
(45) Date of Patent: Apr. 7, 2015

(54) METHOD OF DETECTING PARTICLES BY DETECTING A VARIATION IN SCATTERED RADIATION

(71) Applicant: Xtralis Technologies Ltd, Nassau (BS)

(72) Inventors: Ron Knox, Mount Eliza (AU); Karl Boettger, Elwood (AU); Peter Meikle, Mount Albert (AU); Brian Alexander, Wantirna (AU)

(73) Assignee: Xtralis Technologies Ltd., Nassau (BS)

( * ) Notice: Subject to any disclaimer, the term of this patent is extended or adjusted under 35 U.S.C. 154(b) by 0 days.

(21) Appl. No.: 14/089,315

(22) Filed: Nov. 25, 2013

(65) Prior Publication Data

US 2014/0078297 A1    Mar. 20, 2014

Related U.S. Application Data

(63) Continuation of application No. 13/775,577, filed on Feb. 25, 2013, now Pat. No. 8,620,031, which is a continuation of application No. 13/164,123, filed on Jun. 20, 2011, now Pat. No. 8,406,471, which is a continuation of application No. 10/556,807, filed as application No. PCT/AU2004/000637 on May 14, 2004, now Pat. No. 7,983,445.

(30) Foreign Application Priority Data

May 14, 2003    (AU)    ................................ 2003902319

(51) Int. Cl.
*G06K 9/00*    (2006.01)
*G01N 21/84*    (2006.01)
(Continued)

(52) U.S. Cl.
CPC .............. *G01N 21/84* (2013.01); *G01S 7/4802* (2013.01); *G01S 7/4811* (2013.01); *G01S 7/497* (2013.01);
(Continued)

(58) Field of Classification Search
None
See application file for complete search history.

(56) References Cited

U.S. PATENT DOCUMENTS 3,429,243 A    2/1969    Boyle
3,688,298 A    8/1972    Miller et al.
(Continued)

FOREIGN PATENT DOCUMENTS

DE    36 41 716 A1    6/1988
JP    S5387283 A    8/1978
(Continued)

OTHER PUBLICATIONS

Office Action issued by the US Patent and Trademark Office in counterpart U.S. Appl. No. 11/719,226 dated Jan. 27, 2012.
(Continued)

*Primary Examiner* — Atiba O Fitzpatrick
(74) *Attorney, Agent, or Firm* — Sughrue Mion, PLLC

(57) ABSTRACT

A smoke detecting method which uses a beam of radiation such as a laser (16), to monitor a region, such as a room (12). A camera (14) is used to capture images of part of the room (12), including a path of the laser beam. Particles in the laser beam scatter light (30), and this is captured by the camera (14) for analysis. A processor (20) extracts data relating to the scattered light (30) to determine the density of particles in the beam, to determine the level of smoke in the region. The laser may have a modulated output (38) so that images captured without the laser tuned "on" can be used as a reference point and compared to images taken with the laser turned "on", to assist in determining the level of scattered light (30) compared to ambient light. Filters (24, 26) may be used to decrease signals generated from background light.

20 Claims, 15 Drawing Sheets

(51) Int. Cl.

| | | |
|---|---|---|
| *G01S 7/48* | (2006.01) | |
| *G01S 7/481* | (2006.01) | |
| *G01S 7/497* | (2006.01) | |
| *G01S 17/89* | (2006.01) | |
| *G08B 17/103* | (2006.01) | |
| *G08B 17/107* | (2006.01) | |
| *G08B 17/12* | (2006.01) | |
| *G06K 9/46* | (2006.01) | |
| *G01N 21/53* | (2006.01) | |

(52) U.S. Cl.
CPC ............... *G01S 17/89* (2013.01); *G08B 17/103* (2013.01); *G08B 17/107* (2013.01); *G08B 17/125* (2013.01); *G06K 9/46* (2013.01); *G01N 21/53* (2013.01)

(56) References Cited

U.S. PATENT DOCUMENTS

| | | |
|---|---|---|
| 3,727,056 A | 4/1973 | Enemark |
| 3,737,858 A | 6/1973 | Turner et al. |
| 3,788,742 A | 1/1974 | Garbunny |
| 3,901,602 A | 8/1975 | Gravatt |
| 3,915,575 A | 10/1975 | Sick |
| 3,924,252 A | 12/1975 | Duston |
| 4,594,581 A | 6/1986 | Matoba |
| 5,189,631 A | 2/1993 | Suzuki |
| 5,225,810 A | 7/1993 | Inoue et al. |
| 5,266,798 A | 11/1993 | Borden et al. |
| 5,381,130 A | 1/1995 | Thuillard et al. |
| 5,502,434 A | 3/1996 | Minowa et al. |
| 5,530,433 A | 6/1996 | Morita |
| 5,576,697 A | 11/1996 | Nagashima et al. |
| 5,646,390 A | 7/1997 | Wang et al. |
| 5,696,379 A | 12/1997 | Stock |
| 5,751,785 A | 5/1998 | Moorman et al. |
| 5,861,951 A | 1/1999 | Uesugi et al. |
| 5,912,619 A | 6/1999 | Vogt |
| 5,923,260 A | 7/1999 | Endo et al. |
| 6,091,345 A | 7/2000 | Howard et al. |
| 6,119,055 A | 9/2000 | Richman |
| 6,204,768 B1 | 3/2001 | Kosugi et al. |
| 6,292,683 B1 | 9/2001 | Gupta et al. |
| 6,509,832 B1 | 1/2003 | Bauer et al. |
| 6,658,203 B1 | 12/2003 | Oster |
| 6,813,303 B2 | 11/2004 | Matsuda et al. |
| 7,983,445 B2 | 7/2011 | Knox et al. |
| 8,154,724 B2 | 4/2012 | Mitchell et al. |
| 8,406,471 B2 | 3/2013 | Knox et al. |
| 8,427,642 B2 | 4/2013 | Mitchell et al. |
| 8,508,376 B2 | 8/2013 | Knox et al. |
| 8,620,031 B2 | 12/2013 | Knox et al. |
| 2002/0070854 A1 | 6/2002 | Bartholomew et al. |
| 2002/0080040 A1 | 6/2002 | Schneider et al. |
| 2002/0118352 A1 | 8/2002 | Ohzu et al. |
| 2002/0135490 A1 | 9/2002 | Opitz et al. |
| 2002/0153499 A1 | 10/2002 | Oppelt et al. |
| 2003/0189487 A1 | 10/2003 | Mathews et al. |
| 2004/0017505 A1 | 1/2004 | Yanauchi |
| 2004/0051791 A1 | 3/2004 | Hashimoto |
| 2004/0056765 A1 | 3/2004 | Anderson et al. |
| 2004/0080618 A1 | 4/2004 | Norris et al. |
| 2004/0085448 A1 | 5/2004 | Goto et al. |
| 2005/0207655 A1 | 9/2005 | Chopra et al. |
| 2006/0170787 A1 | 8/2006 | Bentkovski |
| 2006/0202847 A1 | 9/2006 | Oppelt et al. |
| 2007/0024459 A1 | 2/2007 | Cole |
| 2007/0064980 A1 | 3/2007 | Knox et al. |
| 2008/0061250 A1 | 3/2008 | Perel et al. |
| 2008/0297360 A1 | 12/2008 | Knox et al. |
| 2011/0058167 A1 | 3/2011 | Knox et al. |
| 2011/0221889 A1 | 9/2011 | Knox et al. |
| 2011/0243389 A1 | 10/2011 | Knox et al. |
| 2012/0038768 A1 | 2/2012 | Fujimori |
| 2012/0140231 A1 | 6/2012 | Knox et al. |
| 2013/0121546 A1 | 5/2013 | Guissin |
| 2013/0170705 A1 | 7/2013 | Knox et al. |
| 2014/0022547 A1 | 1/2014 | Knox et al. |
| 2014/0028989 A1 | 1/2014 | Butscher et al. |

FOREIGN PATENT DOCUMENTS

| | | |
|---|---|---|
| JP | S5622932 A | 3/1981 |
| JP | 362153780 A | 7/1987 |
| JP | H03245296 A | 10/1991 |
| JP | 5020563 A | 1/1993 |
| JP | 05-288668 A | 11/1993 |
| JP | H06109631 A | 4/1994 |
| JP | H0712724 A | 1/1995 |
| JP | 10154284 | 6/1998 |
| JP | H10232196 A | 9/1998 |
| JP | H11503236 A | 3/1999 |
| JP | 11339150 A | 12/1999 |
| JP | 2000-019112 A | 1/2000 |
| JP | 2000-180349 A | 6/2000 |
| JP | 2002250769 A | 9/2002 |
| JP | 2004-257876 A | 9/2004 |
| WO | 2004/102498 A1 | 11/2004 |
| WO | 2006/050570 A1 | 5/2006 |

OTHER PUBLICATIONS

Office Action issued by the US Patent and Trademark Office in counterpart U.S. Appl. No. 11/719,226 dated May 29, 2012.
Notice of Allowance issued by the US Patent and Trademark Office in counterpart U.S. Appl. No. 11/719,226 dated Apr. 8, 2013.
Office Action issued by the US Patent and Trademark Office in counterpart U.S. Appl. No. 12/743,171 dated Feb. 15, 2012.
Office Action issued by the US Patent and Trademark Office in counterpart U.S. Appl. No. 12/743,171 dated Jan. 14, 2014.
European Search Report issued by the European Patent and Trademark Office in European Patent Application 12183197.8 dated May 10, 2013.
European Search Report issued by the European Patent and Trademark Office in European Patent Application 12183106.9 dated May 15, 2013.
European Search Report issued by the European Patent and Trademark Office in European Patent Application No. 12183148.1 dated Jun. 5, 2013.
European Search Report issued by the European Patent and Trademark Office in European Patent Application No. 12183185.3 dated Jun. 20, 2013.
European Search Report issued by the European Patent and Trademark Office in European Patent Application No. 12183207.5 dated Jul. 2, 2013.
European Search Report issued by the European Patent and Trademark office in European Patent Application No. 08849716.9 dated Nov. 1, 2011.
Office Action dated May 19, 2014 issued in U.S. Appl. No. 12/743,171.
Office Action dated Jan. 7, 2010 issued in U.S. Appl. No. 10/556,807.
Office Action dated Mar. 17, 2009 issued in U.S. Appl. No. 10/556,807.
Office Action dated Aug. 9, 2010 issued in U.S. Appl. No. 10/556,807.
Allowance dated Mar. 15, 2011 issued in U.S. Appl. No. 10/556,807.
Restriction Oct. 19, 2011 issued in U.S. Appl. No. 13/164,123.
Office Action dated May 14, 2012 issued in U.S. Appl. No. 13/164,123.
Allowance dated Nov. 23, 2012 issued in U.S. Appl. No. 13/164,123.
Office Action dated May 8, 2013 issued in U.S. Appl. No. 13/775,577.
Allowance dated Aug. 23, 2013 issued in U.S. Appl. No. 13/775,577.
Office Action dated Jun. 20, 2014 issued in U.S. Appl. No. 13/936,418.
European Search Report Dated Jan. 24, 2013, issued in counterpart European Patent Application No. 12182832.1.
Communication dated Jun. 3, 2014 from The Japanese Patent Office in counterpart Japanese Patent Application No. 2013-055559.
Communication dated Jun. 10, 2014 from The Japanese Patent Office in counterpart Japanese Patent Application No. 2013-096833.
Communication dated Jun. 3, 2014 from The Japanese Patent Office in counterpart Japanese patent Application No. 2010-196936.

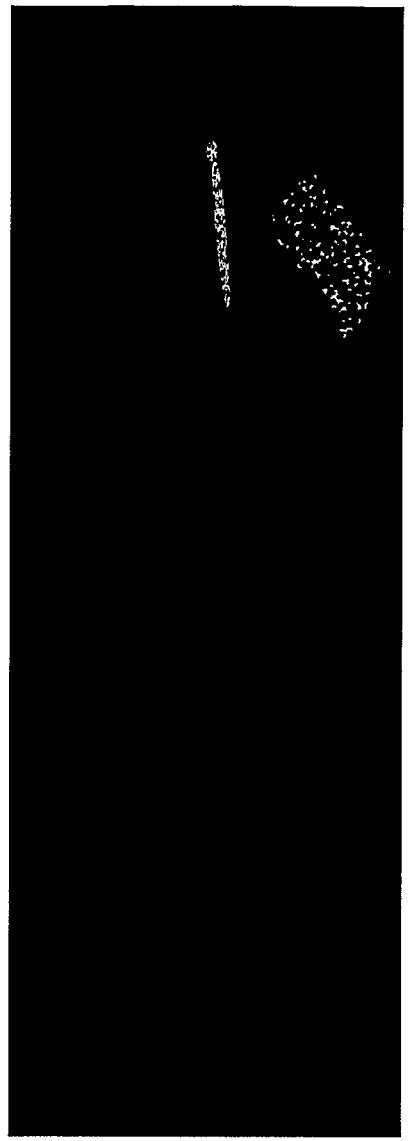

METHOD OF DETECTING PARTICLES BY DETECTING A VARIATION IN SCATTERED RADIATION

CROSS-REFERENCE TO RELATED APPLICATIONS

This is a Continuation application of U.S. application Ser. No. 13/775,577, filed Feb. 25, 2013 which is a Continuation application of U.S. application Ser. No. 13/164,123, filed Jun. 20, 2011 which is a Continuation application of U.S. application Ser. No. 10/556,807, filed Nov. 9, 2006, now U.S. Pat. No. 7,983,445 issued Jul. 19, 2011, which is a U.S. National Stage Application of PCT/AU2004/000637 filed May 14, 2004, which claims priority to Australian Provisional Patent Application No. 5 2003902319, filed 14 May 2003 and entitled "Laser Video Detector". The above-noted applications are incorporated herein by reference in their entirety.

FIELD OF THE INVENTION

The present invention relates to an improved sensor apparatus and improved method of sensing. In particular the present invention relates to an improved particle 10 detector and method of detecting particles.

BACKGROUND OF THE INVENTION

There are a number of ways of detecting smoke in a region, such as a room, building, enclosure, or open space. Some methods involve sampling air from the region and passing the sampled air through a detection chamber, whereby particles are detected and an estimation is made of the amount of smoke in the region of interest. Such an apparatus is exemplified in aspirated smoke detectors like LaserPLUS™ sold by the applicant. Other detectors are placed in the region of interest, and use a sensor to detect particles adjacent the sensor. An example of such a detector is a point detector, in which air passes between an emitter and a sensor, and the smoke is detected directly in the region of interest.

In both cases if the smoke does not enter a sampling point (of the aspirated detector) or pass between the sensor and emitter of the point detector, no smoke will be detected. As many buildings employ air handling means for extracting air from a region, such as air-conditioning, there is no guarantee that smoke will be detected rather than pass out of the region via the air handling ducts. It can be very difficult to use the aforementioned methods of detecting smoke in outdoor areas or very large indoor arenas where there may not be appropriate locations to place a point detector or a sample point and connecting tubing.

Other devices used to detect smoke include the detector disclosed in U.S. Pat. No. 3,924,252, (Duston) which uses a laser and a photodiode to detect light scattered from particles. This device uses a corner reflector to reflect the light back at the emitter. Duston requires a feedback circuit to detect whether the beam is emitted or blocked.

Another type of detector is known as a "Beam Detector", which measures the attenuation of the intensity of a signal from a projected light source caused by smoke particles suspended in the projected light. These detectors have relatively low sensitivity and are only capable of measuring the total attenuation within the illuminated region.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

SUMMARY OF THE INVENTION

In one form the present invention provides a method of detecting particles including emitting a beam of radiation into a monitored region and detecting a variation in images of the region indicating the presence of the particles.

With respect to the above method, further steps embodying the method and features of preferred embodiments may include identifying an area of interest in the images which represents a corresponding zone of the monitored region. Scattered radiation within the zone may be represented in one or more segments of a corresponding image, which allows for the location of the particles in the region to be identified. The location of the particles may be determined in accordance with a geometric relationship between the locations of a source of emitted radiation, a direction of the emitted radiation and a point of image detection wherein, the geometric relationship is determined from the images. The detected variation may be an increase in scattered radiation intensity. The increase in scattered radiation intensity may be assessed with reference to a threshold value. The threshold value may be calculated by averaging integrated intensity values from the images. The method may comprise assigning different threshold values for different spatial positions within the region. The method may comprise directing the radiation along a path and identifying a target in the images, the target representing a position at which the radiation is incident on an objective surface within the region. A location of the target in the images may be monitored and the emission of radiation may be ceased in response to a change in the location of the target. The method comprise identifying a location of an emitter in the images. Further, the method may comprise determining an operating condition of the emitter based on radiation intensity at the identified location of the emitter. The images may be processed as frames which are divided into sections which represent spatial positions within the monitored region. Also, the method may comprise monitoring intensity levels in associated sections of the images and assigning different threshold values for different spatial positions within the region which correspond to the associated sections.

In another aspect, the present invention provides apparatus for monitoring a region, comprising:
an emitter for directing a beam of radiation comprising at least one predetermined characteristic into the region;
an image capture device for obtaining at least one image of the region; and
a processor for analysing the at least one image to detect variation of the at least one characteristic between the images, indicating presence of particles within the region.

The processor may be adapted to determine the location of particles in accordance with a geometric relationship between the locations of the emitter, the directed beam of radiation and the image capture device wherein, the geometric relationship is determined from the analysed images. The apparatus may comprise a plurality of emitters, arranged to direct radiation along different respective beam paths. The apparatus may further comprise one or more filters for adapting the image capture device to capture radiation from the emitter in preference to radiation from other sources. The filters may be one or more or a combination of:

a temporal filter.
a spatial filter.
a band-pass filter.
a polarising filter.

The image capture device preferably comprises an attenuator. The attenuator may comprise a variable aperture device. A plurality of image-capturing devices may be used. Preferably, the image capture device comprises a camera. It is also preferable that the emitter comprises a laser.

In a further aspect, the resent invention provides a method of detecting particles comprising the steps of: determining a path of a beam of radiation comprising placing a first image capturing device to view a source of the radiation and at least a part of the path of the beam of radiation; communicating the position of the source to a processor; placing a second image capturing device to view an impact point of the beam of radiation; communicating related position information of the impact point to the processor; determining the path of the beam in accordance with a geometric relationship between the position of the source and the position information of the impact point.

In yet another aspect the present invention provides a method of detecting particles comprising the steps of determining a region of interest containing a path of a beam of radiation comprising locating a first point, being the position of a source of the beam, using an image capturing device; locating a second point being the intersection of the beam of radiation with a field of view of the image capturing device, determining the path of the beam in accordance with the first and second point; calculating a region of interest containing the determined beam path.

The step of locating a second point may be performed with at least one substantially transparent probe and the probe is preferably removed from the beam path once located.

In still another aspect, the present invention provides a method of determining the level of smoke at one or more subregions in a region of interest comprising: directing a beam of radiation within the region, selecting a view of at least a portion of a path of the beam with an image capture device, determining the location of the source of the radiation relative to the image capture device, determining the direction of the beam relative to the image capture device, dividing the beam of radiation into segments, determining a geometric relationship between the segments and the image capture device, adjusting a level of light received by the image capture device of each segment so as to allow for the geometric relationship. The segments may comprise at least one pixel and the segments are preferably grouped to form the subregions for smoke detection.

In a further aspect the present invention provides apparatus adapted to detect particles, said apparatus comprising processor means adapted to operate in accordance with a predetermined instruction set, said apparatus, in conjunction with said instruction set, being adapted to perform the method as disclosed herein.

In embodiments of the present invention there is provided a computer program product comprising; a computer usable medium having computer readable program code and computer readable system code embodied on said medium for detecting particles within a data processing system, said computer program product comprising; computer readable code within said computer usable medium for performing the method steps as described herein.

Other aspects, advantages and features are disclosed in the specification and/or defined in the appended claims, forming a part of the description of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, improvements, advantages, features and aspects of the present application may be better understood by those skilled in the relevant art by reference to the following description of preferred embodiments taken in conjunction with the accompanying drawings, which are given by way of illustration only, and thus are not limiting to the scope of the present invention, and in which:

FIG. 7a-c shows images illustrating background cancellation performed by the detection system of FIG. 1;

DETAILED DESCRIPTION OF THE INVENTION

Figure 1:
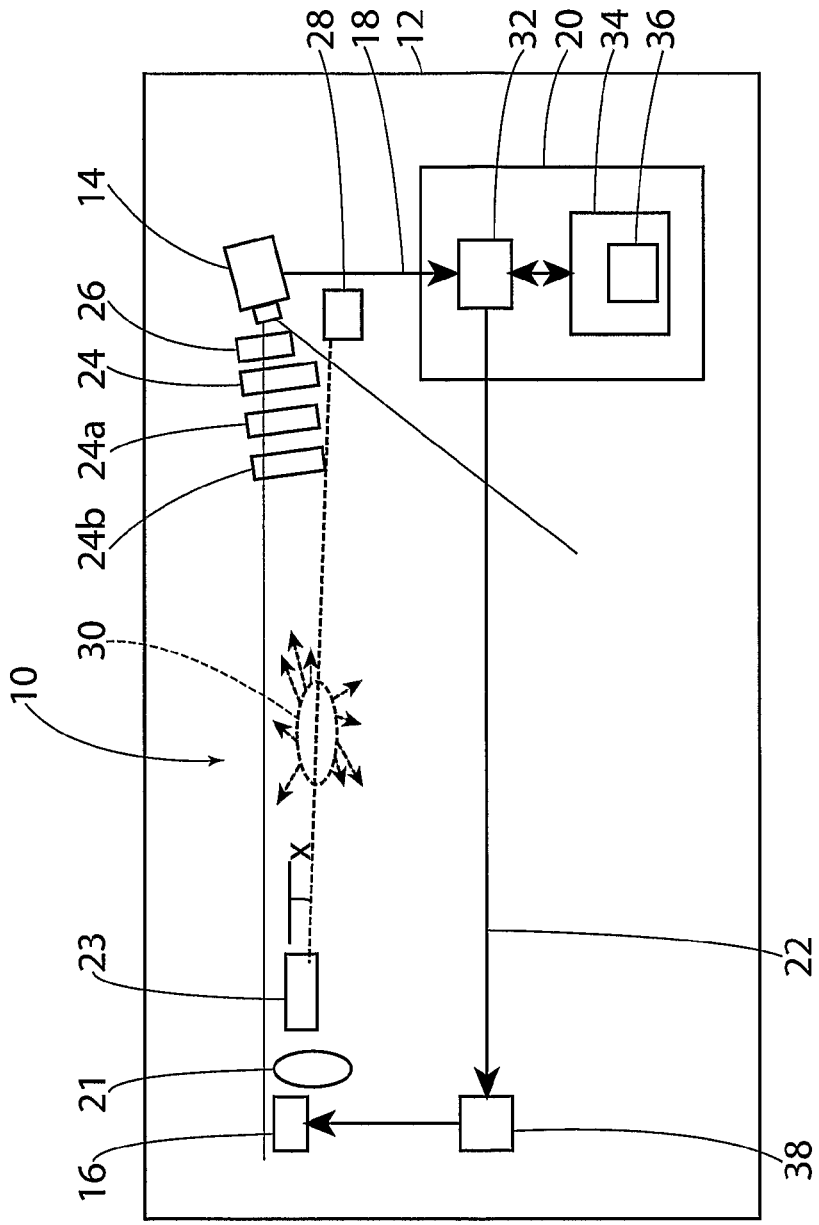
FIG. 1 shows a schematic representation of an embodiment of a detector system 25 from a side view.

In FIG. 1, an embodiment of a particle detector 10 is shown. The detector 10 is located in a region 12 to be monitored. The region could be a room, stadium, hallway, or other area. It is not necessary for the region to be enclosed or indoors.

An image capture device 14 views at least a portion of the region 12, comprising a portion that contains electromagnetic radiation from emitter 16. The image capture device 14 may be a camera or one or more devices forming a directionally sensitive electromagnetic receiver such as photodiodes or CCD's, for example. In the preferred embodiment, the image capture device 14 is a camera. In the present embodiment, the camera 14 uses full frame capture to capture the images to send analogue video information along communications link 18 to a processor 20. It is not necessary to use full frame capture. However, it is preferable to use full frame capture for engineering simplicity in obtaining images, performance, and minimising installation restrictions. As would be understood by the person skilled in the art, other image capture devices 14 such as line transfer cameras may be used and methods to compensate for the efficiency of full frame capture may be employed. Another communication link 22 connects the emitter 16 to the processor 20. The processor 20 controls the output of emitter 16, and/or receives information about the output of emitter 16 through the communications link 22. Alternatively, the state of the emitter 16 may be sensed by the camera 14 or determined automatically as disclosed below. In the preferred embodiment, the emitter 16 is a laser producing visible, infra-red or other suitable radiation. The laser 16 may incorporate a lens 21 and spatial filter such as a field of view restrictor 23. When a beam of light travels thought a homogeneous medium there is no scattering, only when irregularities are present does the beam scatter. Therefore, in the presence of particles such as smoke particles the laser beam will scatter. Furthermore, in accordance with the preferred embodiment, the laser 16 may be modulated, eg "laser on", laser "off" in a given sequence. When no smoke is present, the intensity of pixels in a captured image including the laser beam is the same regardless of the state of the laser. When smoke is present, there is a difference between the intensity of a captured image when the laser 16 is on (due to scattering), compared to the intensity when the laser 16 is turned off.

Optional filters are shown in FIG. 1 in the form of a polarizing filter 24 and a band pass filter 26. The polarising filter 24 is adapted to allow electromagnetic radiation emitted from the emitter 16 to pass through, while preventing some of the background light from entering the camera 14. This is useful if the emitter 16 is a laser emitting polarised light, then the polarising filter 24 can be aligned with the polarisation angle of the laser beam to allow maximum transmission of laser light, while removing some background light, which typically is from randomly or non polarised light sources. The second filter 26 is a band pass filter, which attempts to only allow light within a predetermined frequency range (i.e. the frequency of the electromagnetic radiation from the emitter 16). For example, an interference filter or coloured gel may be used as the band pass filter 26. By using a band pass filter (for example allowing substantially only light around 640 nm if a red laser of that frequency is used), significant background light will be removed, increasing the relative intensity of light scattered from particles suspended in the air in the region 12.

Other filtering methods comprise modulation of the laser and use of positional information with regard to the systems components as described below.

The image capture device may employ an attenuator for controlling the radiation received. A controllable neutral density filter arrangement may be used. Alternatively, the attenuator could be in the form of controlling the intensity with a variable aperture. An optional, adjustable, iris 24a can be used to control exposure levels. It can be manually set at the time of installation, or the system could automatically set the exposure according to incident light levels. The reason for this is to minimise or avoid camera saturation, at least in the parts of the field of view that are used in subsequent processing. The iris 24a could be a mechanical iris or an LCD iris or any other means to reduce the amount of light entering the camera. Some electronic cameras incorporate an electronic shutter, and in this case the shutter time can be used to control exposure instead of an iris 24a. A spatial filter 24b is also shown, which may for example comprise a slit for effectively masking the incident light to the camera 14. For example, a slit may mask the incident received light at the camera 14 to conform generally to the shape of the laser beam as it would be projected in the plane of the camera 14 lens. Items 26, 24a, 24b & 24 can be physically located in a variety of orders or combinations.

In use, electromagnetic radiation, such as a red laser light from emitter 16, passes through the region 12 and impacts on a wall or an absorber 28. The field of view of the camera 14 comprises at least part of the path of the laser, and optionally, the impact point of the laser on the wall, which in this case impacts on an absorber 28. Particles in the air in the region that intersect the laser, in this case represented by particle cloud 30, will cause laser light to scatter. Some of the light scattered from particles will fall on the sensor of the camera 14, and be detected.

In the embodiment shown in FIG. 1 the camera 14 outputs analogue information to a video capture card 32 of the processor 20. The video capture card 32 converts the analogue information to digital information which is then further processed by computer 34. The processing is undertaken by software 36 running on the computer 34, which will be described later. In the preferred embodiment, the processing is carried out in order to interpret the captured image(s) such that an image plane corresponds to or is mapped to corresponding positions on the laser beam. This may be achieved by relatively straightforward geometry and trigonometry once predetermined location or position information of the system's components is obtained.

In other embodiments it is possible to use a camera 14 which would capture the data and transmit it digitally to the processor 20 without the need for a video capture card 32. Further, the camera 14, filters 24, 26, processor 20 and light source 16 could be integrated into a single unit or units. Also, embedded systems may be employed to provide the functions of at least the processor 20.

A number of camera 14 configurations are able to be used in this application, provided image information in the form of data can be supplied to the processor 20.

In the example shown in FIG. 1, a laser modulator 38 is used to vary the power of the emitter 16. The power level can be changed to suit lighting conditions, meet eye safety requirements and provide on/off modulation. In this embodiment, the camera 14 captures 30 frames every second, the emitter 16 is cycled on for one frame and off for the next. The amount of light in a region is sensed for each frame, and the sum of the light in a region when the laser is off is subtracted from the sum of light received while the laser is on. The sums may be over several frames. The difference between the sum of light received when the laser is on compared to the light received when the laser is off is taken as a measure of the amount of scattering in that region. To act as an alarm, a threshold difference is set and should the difference be exceeded, the alarm may be activated. In this way the detector 10 may act as a particle detector. As measuring the scattered light from particles is known to be a method of determining whether there is smoke in a region, the detector 10 may be used as a smoke detector. More detail on the cancellation, filtering and software is provided below.

The detector 10 may be set to wait until the measured scattering exceeds a given threshold for a predetermined period of time, before indicating an alarm or pre-alarm condition. The manner for determining an alarm or pre-alarm condition for the detector 10 may be similar to the methods used in aspirated smoke detectors using a laser in a chamber, such as the VESDA™ LaserPLUS™ smoke detector sold by Vision Fire and Security Pty Ltd.

Figure 2:
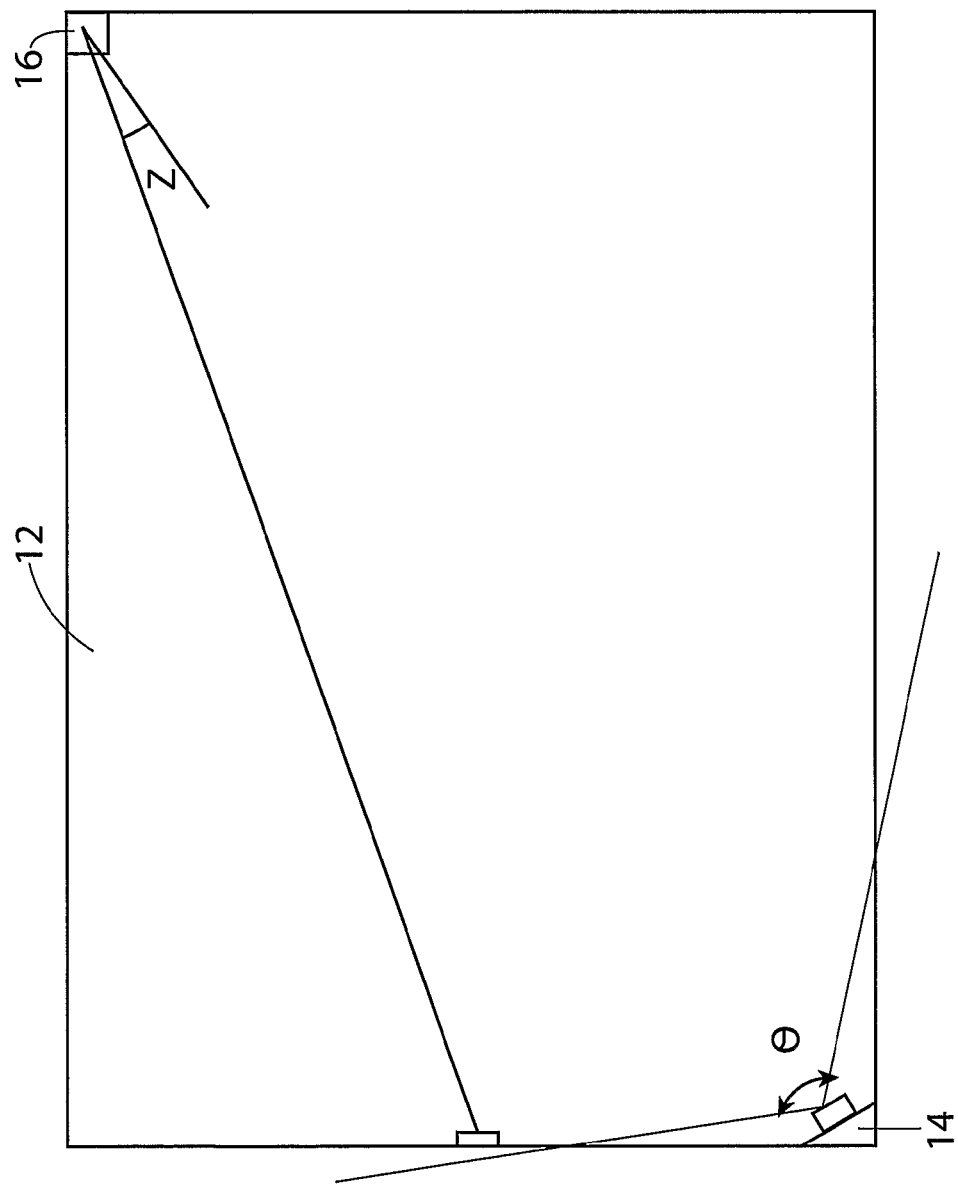
FIG. 2 shows a top plan view of an embodiment of an image capture device and emitter position of the detector system of FIG. 1.
Figure 3:
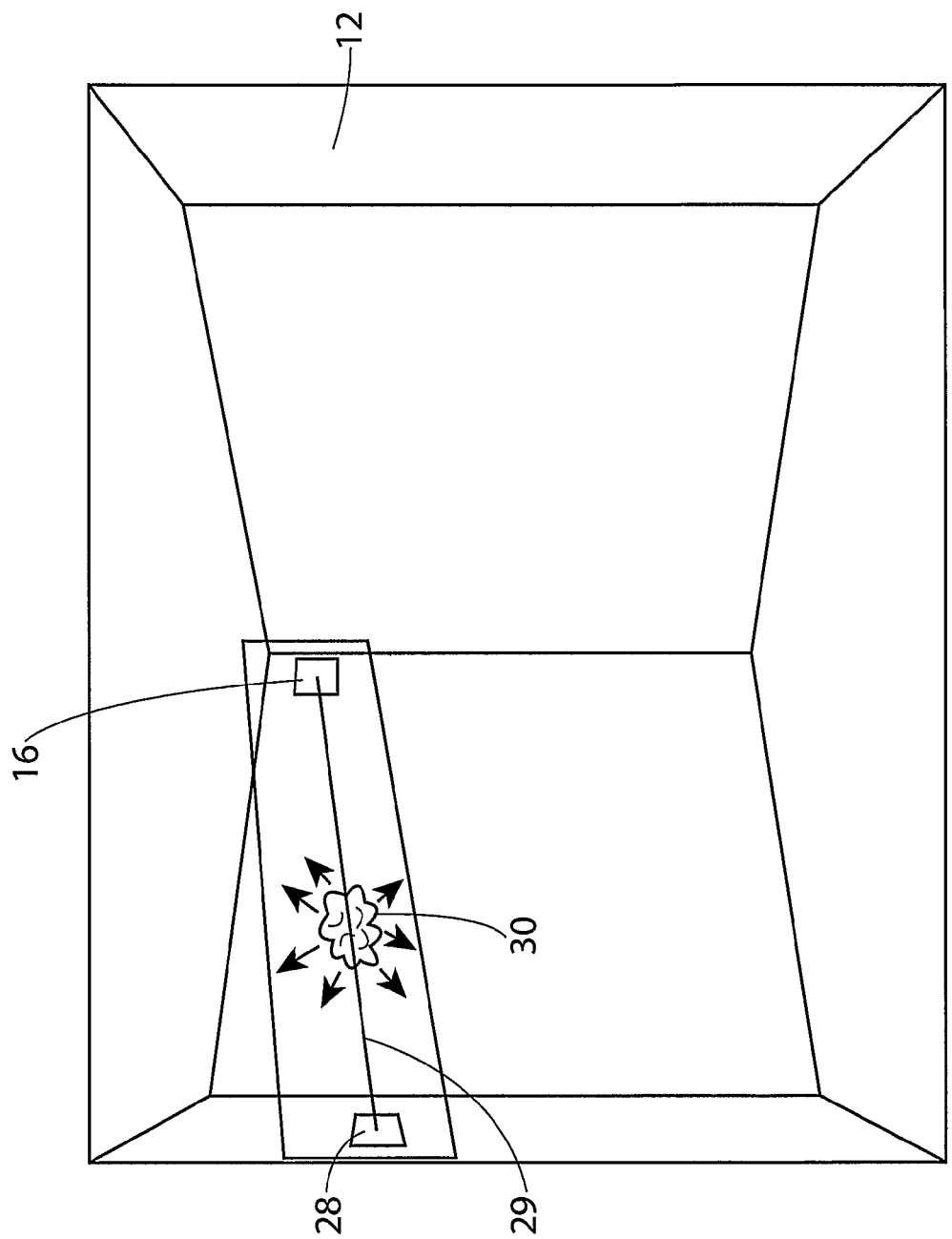
FIG. 3 shows a schematic perspective representation of an image taken by an image capture device of FIG. 2.

FIG. 2 shows a top view of the embodiment in FIG. 1. The camera 14 has a field of view 8, which in this case covers substantially all the region 12, which may be a room in a building. The light from emitter 16 is directed generally towards the camera 14, but not directly at the lens. There is therefore an angle subtended by an imaginary line between the camera 14 and the emitter 16, and the direction of the laser beam. The angle may be in the horizontal plane as shown by angle z in FIG. 2, and/or the vertical plane as shown by angle x. in FIG. 1. The laser beam does not impact on the camera lens directly. Nonetheless, the laser beam path will be in the field of view of the camera 14, as shown in FIG. 3.

Physical System Variations

It is desirable in some circumstances to use a number of emitters in a system. This may be to comply with regulations, provide back up, or to assist in covering a larger area than could be covered with a single emitter.

Figure 9:
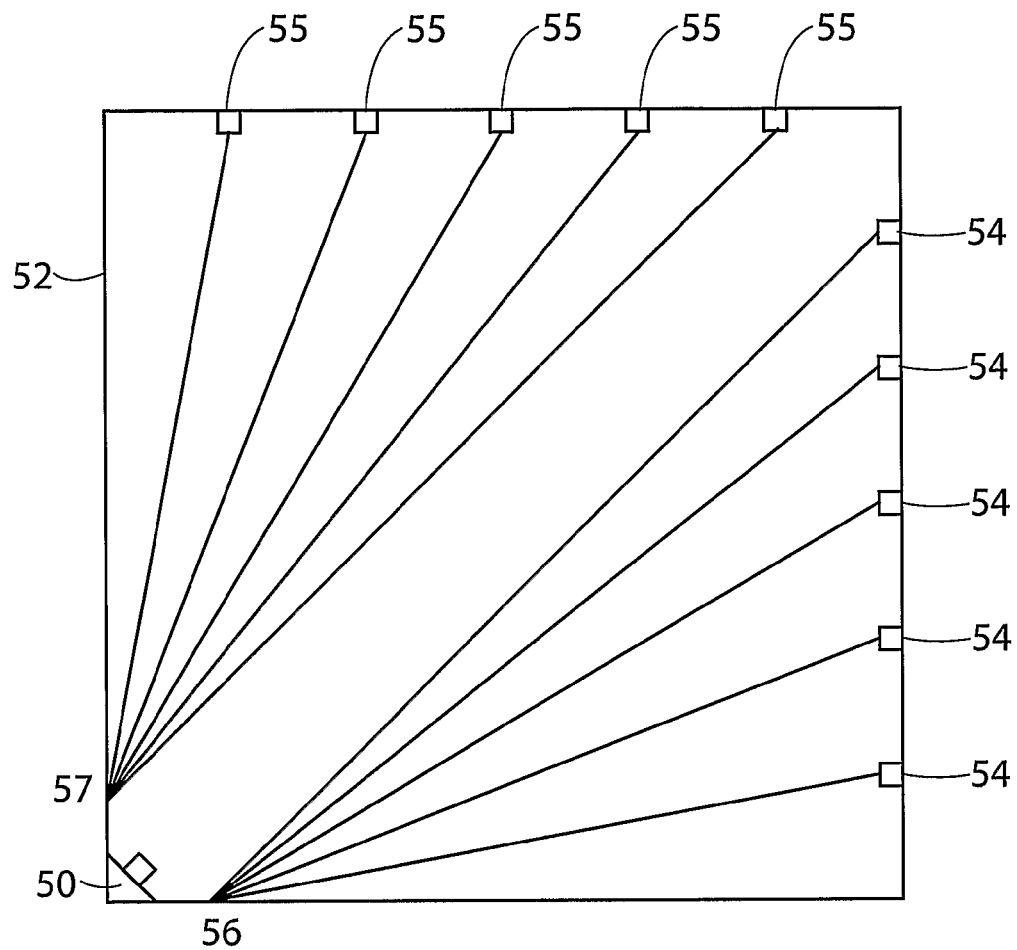
FIG. 9 is a top plan schematic view of a second embodiment of a detector system in accordance with the present invention.

If coverage of a large area is required, it is possible to employ a number of emitters so that smoke may be detected in a number of different locations within a region. FIG. 9 shows an arrangement whereby camera 50 is located within a region such a room 52. If detection was required across a large area, multiple lasers 54 and 55 could be spread around the room to provide coverage. FIG. 9 shows the emitters grouped into two groups, with emitters from group 54 targeted at point 56 and emitters 55 targeted at point 57. The camera 50 may have the points 56 and 57 in view, or may not see the points 56 and 57. Camera 50 may have points 56 and 57 in view by way of an optical arrangement to project an image of points 56 and 57 into the field of view of camera 50, for example, rear view mirrors (not shown) placed forward of camera 50. Likewise a prism or some other optical system could achieve this result. Further, the emitters 54 and 55 may all be on simultaneously, or may be cycled, so that if the camera 50 can detect the point at which the radiation lands, the radiation detected in the camera can be used to verify that the emitter is operating and not blocked. Detection of individual emitters is possible if they were switched on and off sequentially, or in any sequence of patterns that are not linearly dependant, so that using timing information, it is possible to detect which emitter is on at any one time. Further, knowing which emitter was firing would allow the detector to localise sub regions in the area to be protected and ascertain where any detected particles were located with respect to the sub regions. In effect the beam or beams that have been scattered by particles may be determined.

The emitters 54 and 55 do not all need to intersect on targets 56 and 57, and may be distributed along a number of targets, or cross over each other onto other targets.

Figure 10:
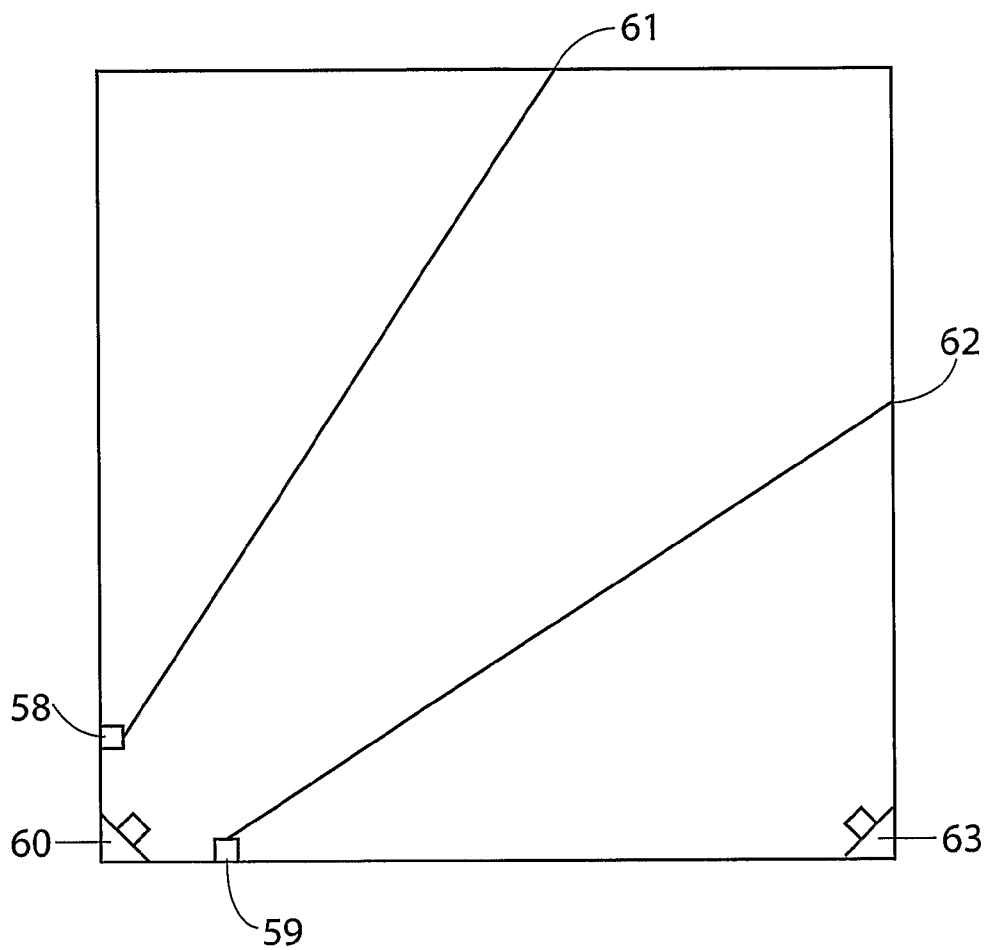
FIG. 10 is a top plan schematic view of a third embodiment of a detector system in accordance with the present invention.

An alternative is shown in FIG. 10, where the lasers 58 and 59 are aimed away from the camera 60. The camera 60 can detect a light from the laser light hitting the wall at point 61 and 62. If either of these points disappears, then the detector system knows that either a laser is faulty or something is blocking the path of the laser light. If the laser is blocked, generally the object blocking the laser light will also reflect the light, and therefore the laser spot will shift from the mown target area, that is original point 61 or 62. The camera can detect the shift in the spot and may sound an alarm or turn the laser off. This may be important, especially if the laser is not considered eye safe. Another means by which faults may be detected is when a spurious object such as a spider web intersects with a beam causing scattering. Occasional movement of the emitted beam, for example by translating the emitter in a lateral direction, will obviate such false detections of scattered radiation.

In FIG. 10 a second camera 63 is shown which may be connected to the system to provide additional views. Using two cameras may allow a more accurate means of locating the area of smoke than using a single camera. Also, the additional view will provide scattering information for different scattering angles for the same particulate material. This data can be used to discriminate between materials with different particle size distributions or scattering properties. This in turn can be used to reduce the system sensitivity to nuisance particles that might otherwise cause false alarms such as dust, for example. With the use of one or more emitters, variation in scattering angle; wavelength of emitted radiation; polarisation rotation; plane of polarisation of viewed scattering and varying the timing of emission and detection all provide means for discriminating between different types of particles.

Figure 11B:
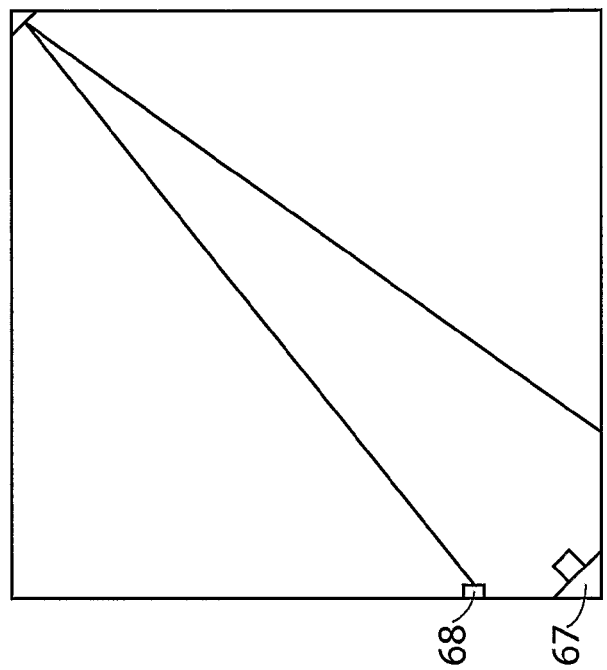
FIGS. 11a-c are top plan schematic views of fourth, fifth and sixth embodiments of the detector system in accordance with the present invention.
Figure 11A:
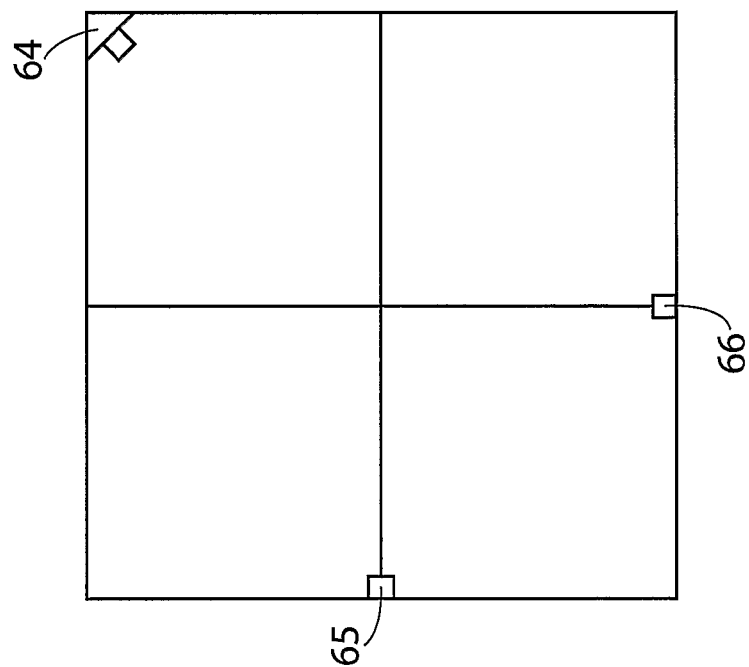

In FIG. 11a camera 64 views two lasers 65 and 66 that cross the room. FIG. 11b uses a laser that is reflected back towards the camera 67, to provide better room 30 coverage and capture both forward and backward scattered light.

In the present embodiment, the processor 10 comprises a personal computer running a Pentium 4 chip, Windows 2000 operating system.

An important aspect of the present embodiments is signal processing is discussed in detail below with reference to FIG. 4 which is a data flow diagram, the layout of which, would be understood by the person skilled in the art. For ease of reference, the signal processing in this embodiment is conducted using software for the detector 10, referred to as LVSD software. It is to be noted with reference to FIG. 4 that the data flow lines indicate image data flow, array data flow and simple numeric or structured data flow at different stages of the processing. Thus, some of the processing functions described may handle the more intensive image data or optionally, the less intensive numeric data, for example. As would be understood by the person skilled in the art, engineering efficiencies may be attained by choice of the components and software entities used to carry out the processing functions at these respective stages.

Laser State Determination

Figure 4:
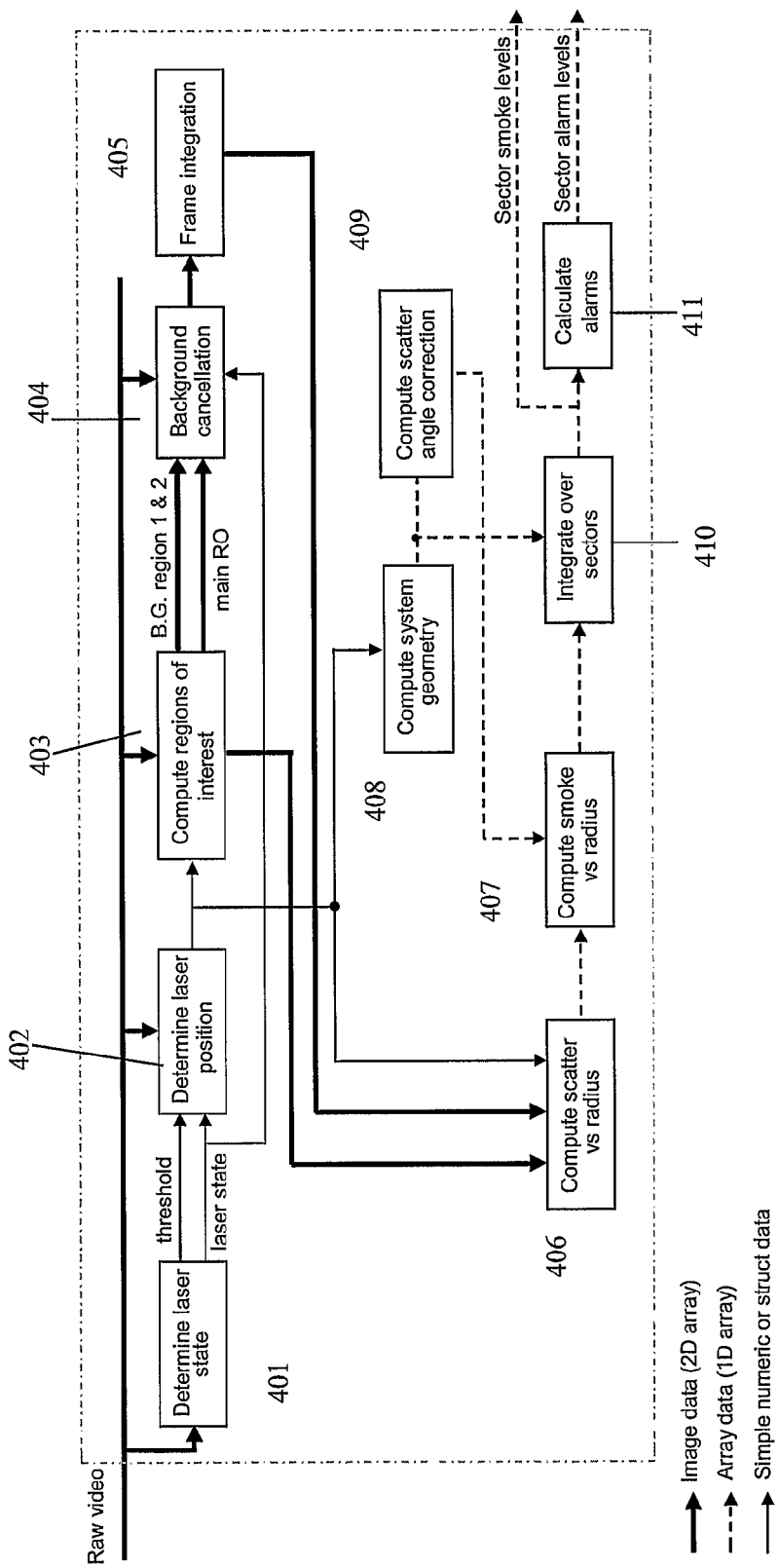
FIG. 4 shows a system overview workflow for signal processing for the detector system of FIG. 1.

At step 401 of FIG. 4 a determination of the laser state is performed. The LVSD software in this embodiment relies on having the laser source within the field of view of the camera in order to determine the state of the laser for a particular frame.

A small region of interest is assigned that includes the laser source radiation. The centre of the region is set to an initial position of the laser source spot. The average pixel value in the region is computed. It is then compared with a threshold value to make the decision of whether the image records the laser on or off.

The threshold value is the average of the outputs of a peak detector and a trough detector that are fed by the average. Each detector executes an exponential decay back to the current average in the case that a new peak or trough has not been made. The time constant is set in terms of frames, preferably with values of about 10.

This technique has proven to be fairly robust. An alternative method is to look for one or more pixels that exceeded the average in the rectangle by a fixed threshold.

In an implementation where the laser on/off switching is more closely coupled to frame acquisition this function may not be required. However, it can still serve a double check that the laser source is not obscured and is of the correct intensity.

Laser Position

At step 401 of FIG. 4, a centre of gravity algorithm estimates the pixel coordinates of the laser source within the area being monitored. This positional information is optionally updated at every "laser on" image to allow for drift in either the laser source or camera location due to movement of the mounts and/or building over time. The factors affecting the stability comprise movement of walls within the building, mounting point rigidity etc.

More precisely, the threshold established in the previous step (laser state determination) is subtracted from the image and negatives are clipped to zero. The centre of gravity of the same rectangle used in the state determination then yields (x,y) coordinates of the laser spot. In this calculation, the pixel values are treated as weight.

An alternative technique is to treat the previously described area as an image and calculate an average of a large number (~50) of known "emitter off state" images, then subtract the average from the latest image that is known to have been captured with the emitter on. The previously described centre of gravity algorithm is then applied to the image data to estimate the position of the spot.

Compute Regions of Interest & Background Cancellation

Figure 5:
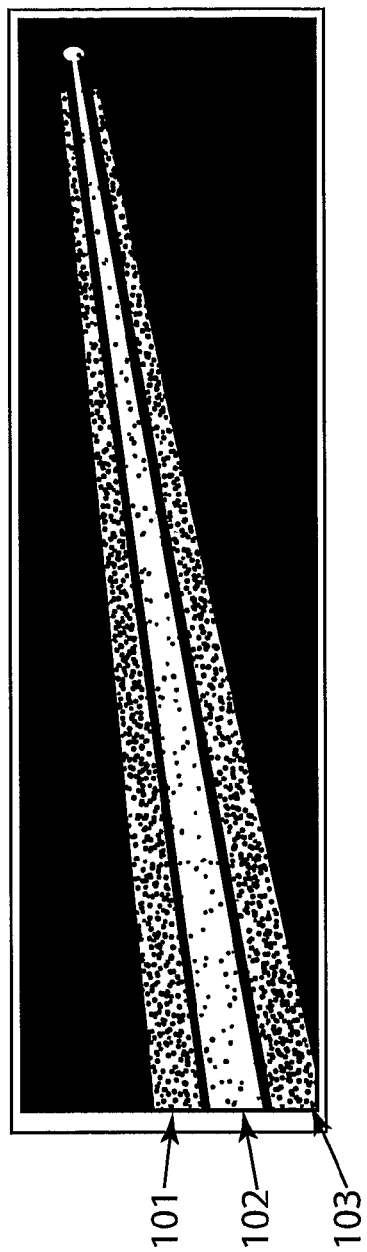
FIG. 5 shows a graphical representation of segmentation of data captured by the image capture device in the embodiment of FIG. 1.

At step 403 of FIG. 4, regions of interest are calculated. At step 404 of FIG. 4, background cancellation is performed. A combination of interpolation and frame subtraction is used during background cancellation to reduce interfering temporally variant and invariant information from the image. The image is segmented into three regions of interest as shown in FIG. 5. The background is segmented into background regions 101 and 103, and there is an integration region 102. These regions are updated periodically to reflect any detected changes in the laser source location. The choice of shape of the regions of interest reflects the uncertainty in the precise position in the image of the scattered radiation. in FIG. 5 the camera cannot see the point where the emitted radiation hits the wall, and therefore the exact path of the emitted radiation is unknown. This produces a region of interest 102 that expands as the distance from the emitter increases. A method of determining the path of the emitted radiation manually is to test the location of the emitted radiation by blocking the radiation temporarily and checking its position, then entering the data manually into the processor. Alternatively, one or more substantially transparent probes, which may be in the form of articles such as plates, may be inserted into the beam. Some scattering will occur on entry and exit from the plate providing a reference point or points in the image from which the required integration area and background areas may be computed. In applications where the detector may be used for detecting particles in, for example, clean room or hazardous environments, the windows of such enclosures may act as the substantially transparent plates and, these therefore may establish the path of the beam without the need to intrude into the environments to install the detector system components. The purpose of a narrow integration area is to reduce the noise contributions from pixels that are not contributing a scattering signal and also to allow the background regions to be closer to the integration region thus allowing a better estimate of the correction factor that is used for correcting the illumination level in the laser off images.

The integration region 102 contains the emitted radiation path, while the areas to each side, background region 101 and 103, are used during background cancellation. The regions are generally triangular, that is wider further away from the laser source. This is necessary because while the exact location of the radiation spot is known, the exact angle of the path is not, so a greater tolerance is needed at the other end of the path when the camera cannot see where the radiation terminates. There is more noise in a fatter section of integration region due to more pixels, fortunately, each pixel represents a shorter length of the path, so the larger number of samples per unit length allows more averaging. If the camera can see the radiation termination point, there would be less uncertainty of its position and the regions of interest would not need to diverge as much as shown in FIG. 5.

Two background regions 101, 103 are chosen for interpolation of the brightness compensation factor for correcting temporal variations in background lighting on either side of the radiation path in the laser off images. For example, changes in lighting due to two different, independent temporally varying light sources on either side of the radiation path. This principle could be further extended to allow for variations along the path, not just to either side of the path by subdividing the three areas 101, 102, 103 into segments along the length of the radiation path and performing the calculations for each subdivision.

Figure 6:
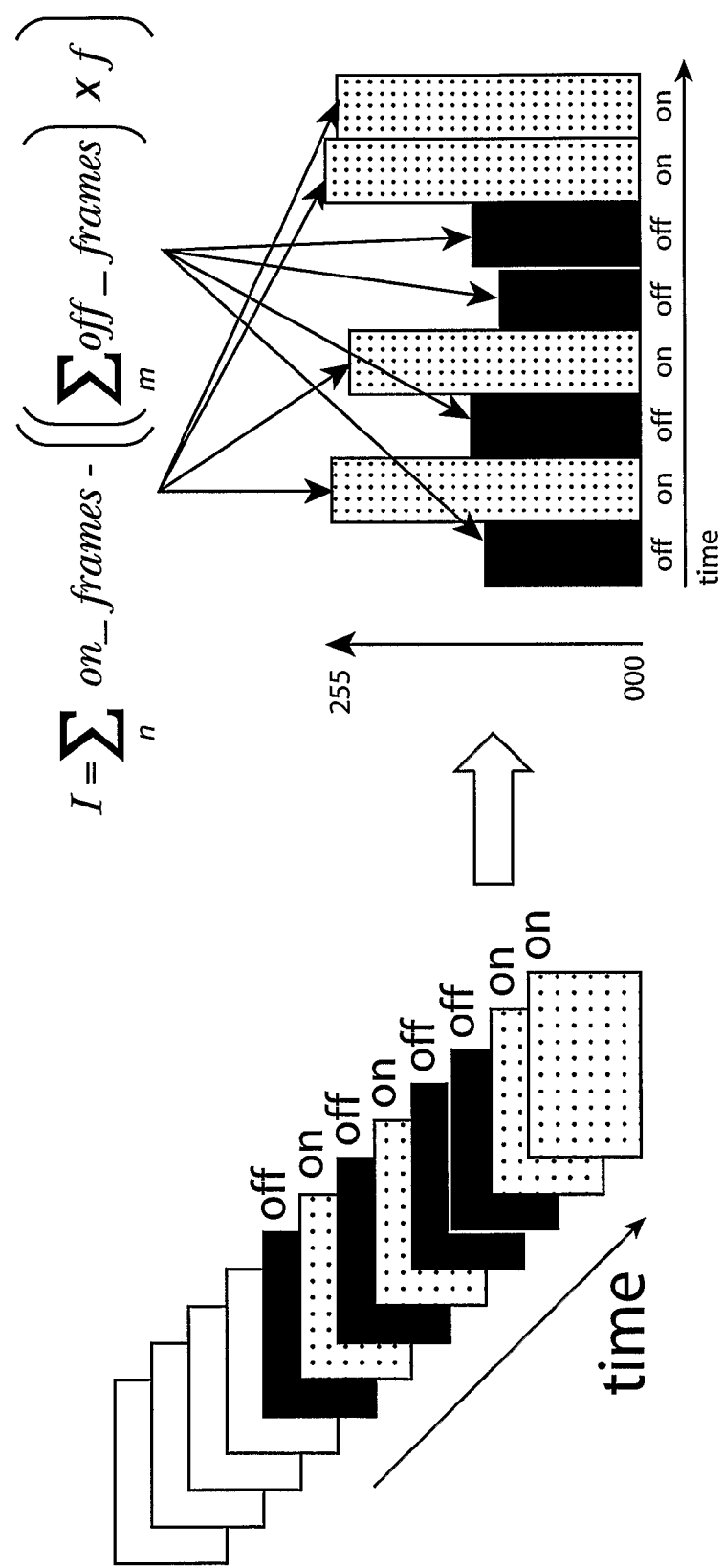
FIG. 6 shows a graphical representation of the integration of the data captured by the image capture device of the embodiment of FIG. 1.

The background cancelling algorithm sums n "on frames" and m "off frames"—the sequence of these frames is arbitrary. Prior to the subtraction of the "emitter off" frames from the "emitter on" frames, the "emitter off" frames are scaled by a factor, f, to compensate for variance in lumination levels of the images. This may be useful with artificial lighting, the intensity of which varies rapidly. The resultant image contains any differences between the n "emitter on" and M "emitter off" images. This is shown graphically in FIG. 6.

The scaling factor f is determined by interpolation, using the ratios of background variation between the laser on and laser off frames.

$$f = \frac{\left(\frac{\mu_{on1}}{\mu_{off1}} + \frac{\mu_{on2}}{\mu_{off2}}\right)}{2}$$

where:

μ is the average value of pixel intensity in a given background region in either a laser on or laser off frame as designated by the subscripts.

If the processor is not fast enough to keep up with the full frame rate, there needs to be a scheme to allow a random selection of frames to be processed. Since n laser on and in laser off frames are used for the background cancellation, while waiting to accumulate this number of frames, any excess laser on or laser off frames can be discarded.

Alliteratively a lock step synchronisation technique could be used so that the computer was fed information about the state of the laser with respect to the captured image. In any case, a minimum of one on frame and one off frame is required for the technique to work.

An alternative to the cancellation scheme described above is to simply subtract laser on and laser off frames. Many on frames and off frames can be summed or averaged or low pass filtered, with the summing, averaging or filtering performed before and/or after the subtraction.

The result of the background cancellation is an image that is predominantly composed of scattered light from the emitter, and some residual background light and noise.

Frame Integration

At step 405 of FIG. 4 frame integration is performed. A number of background cancelled frames are summed, averaged or otherwise low pass filtered to obtain a scattered light image with reduced noise. By averaging a number of frames, interference that is not correlated with the laser on/off switching is reduced and the wanted (correlated) scattering information is retained. Typically the total number of frames used in the background cancellation and frame integration steps is approximately 100 (i.e. approximately 3 seconds of video). Longer periods of integration or lower filter cut-off frequencies may yield an improved signal to noise ratio, and allow a higher sensitivity system at the expense of response time.

Figure 7A:
Figure 7B:
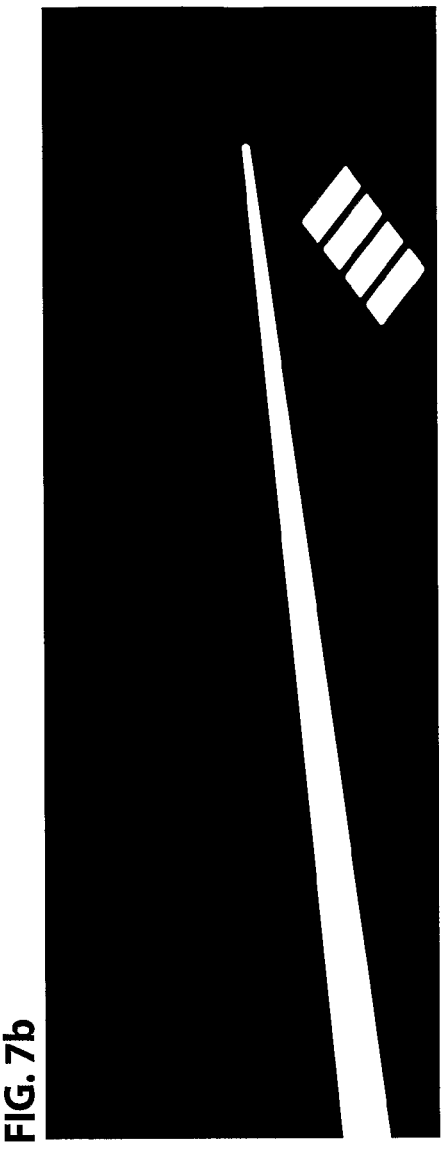

With reference to FIGS. 7a to 7c, the sequence of images shows the effect of background cancellation and integration in the detection of the scattered light. The image intensity has been scaled to allow for better visibility to the eye. The particle obscuration level over the entire beam was approximately 0.15% per meter as measured by a VESDA™ LaserPLUS™ detector, sold by the applicant. FIG. 7a shows the raw video, FIG. 7b highlights the region of integration, and FIG. 7c the scattered light in the presence of smoke after background cancellation and integration.

Scatter Vs Radius Computation

Figure 8:
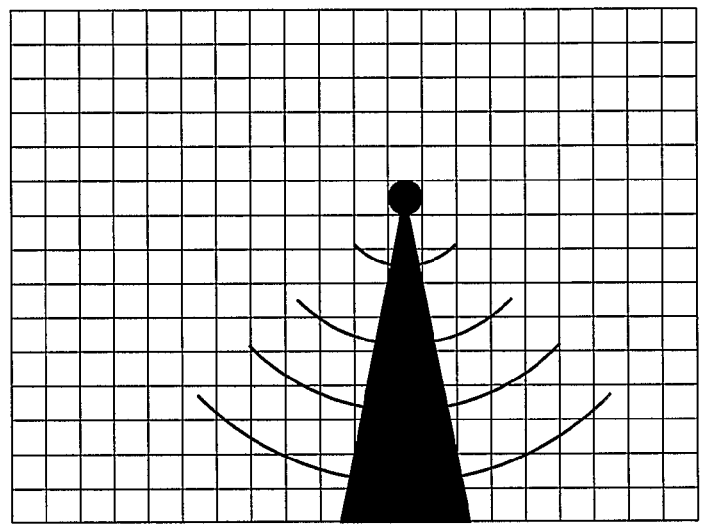
FIG. 8 shows a graphical representation of a method used for calculating pixel radius in an embodiment of the software used in conjunction with the operation of the detector system of FIG. 1.

At step 406 of FIG. 4 computation of the scatter as a function of the radius from the emitter is performed. Variations in intensity along the beam due to system geometry and scattering may be remedied using this method. A data array is calculated containing scattered light levels in the integration region versus radius, for example measured in pixels in the captured image. Since a radius arc covers a number of pixels inside the integration, the intensity of each pixel within a given radius interval is summed together. FIG. 8 is a graphical representation of how the integration region is segmented by arcs centred with respect to the emitter. In FIG. 8, triangle 80 represents the expected integration area and the arcs represent different radii from the laser source. Each portion of the integration area lying between a pair of arcs has its pixels summed and the sum is entered into the scattered light data array. For pixels that are not clearly between two of the arcs, rounding or truncation of the calculated radius corresponding to such pixels can be used to resolve the ambiguity.

Compute Geometry

Figure 12:
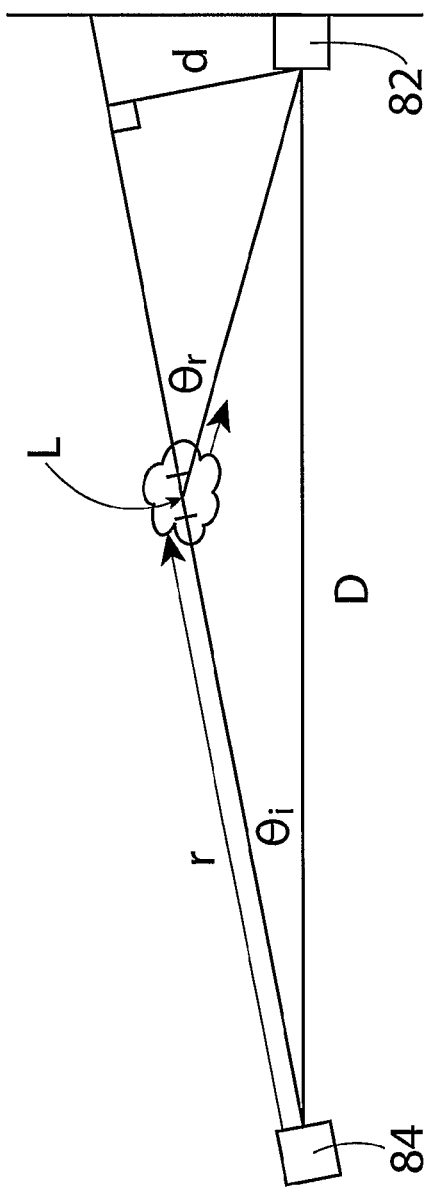
FIG. 12 shows a schematic representation of a part of the detector system of FIG. 1.

At step 408 of FIG. 4, the geometry of the system elements/components is determined. Each pixel as described above (or image point) corresponds to a specific geometric configuration with respect to a scattering volume and the general case of such an image point is shown in FIG. 12. At each such point or pixel, the following parameters can therefore be determined:

θ—scattering angle.
r—the distance in meters from the laser source.
D—distance from camera to laser source.
L—physical length viewed by one pixel at a given point along the beam.

A corrected intensity of pixels corresponding to a given radius, r, is then determined for a real world system, in which the intensity of pixels is multiplied by a predetermined scattering gain value, discussed below under Scattering Angle Correction, corresponding to the given radius and a given scattering angle relative to a lossless isotropic scattering calculation. A resultant scattered data array is formed.

Scattering Angle Correction

A correction for scatter angle is logically determined in accordance with step 409 of FIG. 4. As an input, the program requires a scattering data file, which contains for a given material, the scattering angle and its corresponding gain. The data in this file is generated by an empirical calibration process, and is intended to contain average values for a variety of smoke types.

At each scattering angle as determined during the above geometry computation, the gain for every scattering angle is derived. The data from the input scattering data file is linearly interpolated so that for every scattering angle an approximation of the forward gain can be calculated.

Compute Smoke vs Radius

A determination of smoke for a given radius of the beam is performed at step 407 of FIG. 4. To convert the scattered data array to smoke levels on a per pixel basis requires input of data D, d and $\theta_i$, as shown in FIG. 12. Any combination of lengths or angles that constrain the geometry can also be used. D is the distance from the camera 82 to the emitter 84, $\theta_i$ is the angle made between the line from camera 82 and the emitter 84 and the line corresponding to the path of the radiation from the emitter 84, and d is the length of the line perpendicular to the emitted radiation that intersects the camera entrance pupil. From this information, all other necessary information can be determined by trigonometry and geometry. The geometry can be seen in FIG. 12.

For each element in the previously described Scatter vs Radius array, the values of L, θ and r, as shown in FIG. 12, are computed. L is the length of the beam that is visible to one camera pixel.

Integrate Along Beam to Obtain Obscuration

At step 410 of FIG. 4, integration over beam image sectors is performed to obtain the detected obscuration. The beam length is divided into a number of sectors to provide addressability along the beam. In order to distinguish between the laser source and scattering of the laser beam, the pixels around the laser spot location cannot be included as part of a sector, as the intensity caused by scattering cannot be resolved, especially for an uncollimated source for which flaring may occur causing residual intensity in the pixels surrounding the source.

Likewise at the camera end, due to the geometry of the set up, the field of view of the camera allows the beam to be viewed to within a few meters of the camera.

In order to provide a smooth transition between sector boundaries, a simple moving average filter is implemented. In fact, the beam is divided into n+1 segments, and then a moving average is applied (of length two segments) resulting in n sectors.

Each pixel along the beam captured image corresponds to a physical length along the beam see FIGS. 8 and 12. This physical length gets smaller as the beam approaches the camera. So starting at the laser end and ignoring the pixels that are outside the end boundaries, the obscuration for a particular sector is the sum of all the pixel intensities after the application of the correction noted above, which fall into the physical length and position as described by that sector.

For example, to determine the obscuration, 0, over the whole beam, given as a sector size in pixel radius, r, as n to m, $$O = \frac{\sum_{r=m}^{r=n} S(r)L(r)}{\sum_{r=m}^{r=N} L(r)}$$

where S is scattered light and L is given above.

Figure 13:
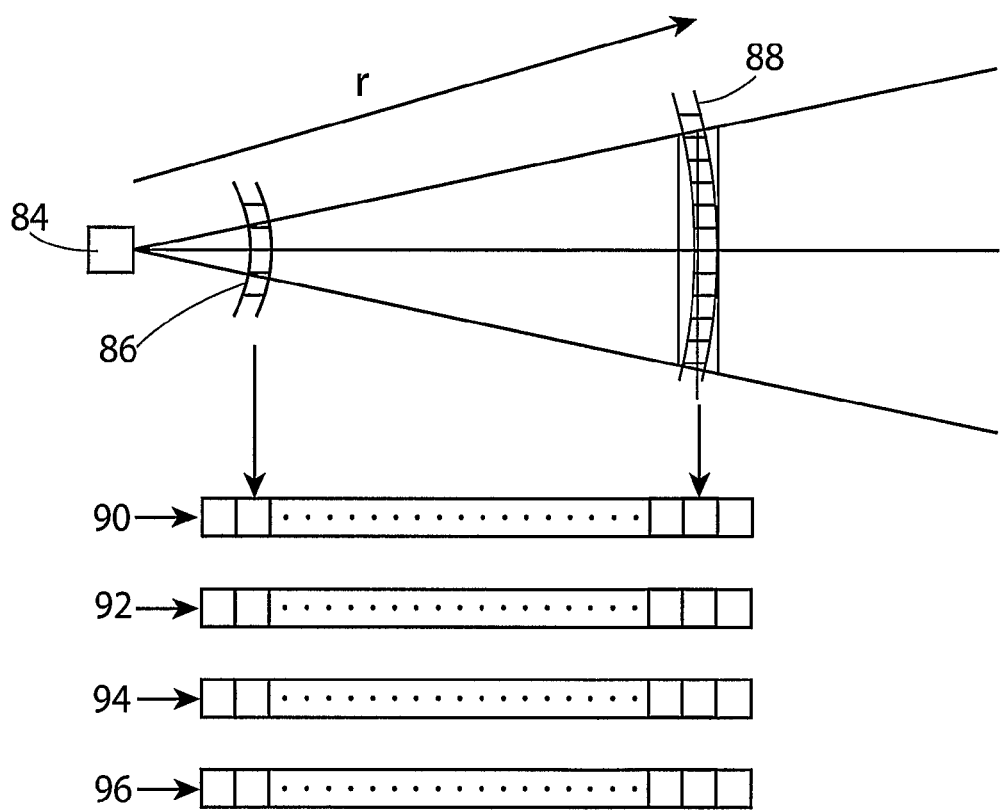
FIG. 13 shows a schematic representation of captured image data from an image capture device of the detector system of FIG. 1.

As noted above, the beam length is divided into a number of segments to determine individual smoke levels for each segment effectively simulating a number of point detectors. The output of these notional point detectors can be provided to an addressable fire panel. This is based on the theory that scattered light emitted from each segment of the emitted radiation will provide a different light output for a given particle density based upon the angle from the radiation path to the camera and the number of pixels per segment. As the path of the emitted radiation comes closer to the camera that is as r increases in FIG. 12 the angle $\theta_r$ increases. The number of pixels that contain scattered light will also increase due to the apparent widening of the beam in the direction towards the camera 82. This increase in width is shown in FIG. 8 and FIG. 13. FIG. 13 shows the emitted radiation from emitter 84. The angle of the radiation spread is amplified for clarity. As the emitted radiation travels further from the emitter (that is as r increases), the number of pixels that coincide with the location of potential scattered radiation increases. At the radius 86, close to the emitter, only two pixels are determined to be within the region of interest covered by the detector, and the light from these pixels is summed and placed into an array 90, being scattered light(r), which comprises a n times 1 array of information, where n is the number of pixels across the screen. At radius 88, many more pixels are within the area of interest covered by the detector, and they are all summed to obtain the amount of scattering obtained within the covered region of interest. Calculated at array 92 is the scattering radiation angle $\theta_r$, which will be different for each pixel. That is, when r is small, $\theta_r$ will be small, and as r increases, so does $\theta_r$. This information is important, as particles of interest in detecting certain events can have different scattering characteristics. Very small particles (relative to the wavelength of the emitted radiation) scatter more uniformly regardless of $\theta_r$ (scattering angle), however larger particles scatter more in the forward direction, and reduce intensity as the angle Or increases. Quite often the particles of interest, in this example smoke particles, are relatively large particles and therefore it can be useful to employ a table of effective scaling factors of output of light for given scattering angles $\theta_r$. Such tables are known in the use of smoke detectors using laser chambers to detect particles.

Array 94 contains the actual radius of the light captured by the pixels. Array 96 comprises the length of the segment of the emitted radiation encompassed by, in this case, one horizontal pixel in the captured image in the frame of the camera. This information is used to ascertain the volume of the emitted radiation and is used to assist in the calculation of the radiation intensity. Also, array 96 contains data on the smoke intensity at each point r, defined as smoke [r].

Alarm State

Finally with reference to FIG. 4, alarm states are calculated. The alarm states for each sector are determined based on thresholds and delays and a priority encoding scheme, as per standard aspirated smoke detectors, or other parameters determined by the user.

The same method is used for the zone alarm level, except that final zone output is the highest sector or the zone level, whichever is higher.

Fault Detection

The system may have provision for the detection of a fault condition, which is essentially the absence of the laser spot in the image. The laser on/off signal duty cycle may be checked to be within 33% to 66% over the number of frames used in one background cancellation cycle.

Alternative Embodiments

A number of alternative embodiments are available, depending on application and desired features. Unless otherwise specified, the general principles of operation as described above apply to the implementation of the following variations. For example, fault detection may be carried out in a number of ways.

In another application, the system described above could be used in applications where measurement of obscuration was important, such as airports where fog may cause planes to divert if visibility falls below a certain level. The system does not require ambient light to operate, and can therefore operate at night without additional lighting. An infrared camera could also be used with an infrared light source, where the light source, if of similar frequency to the detecting light, could be cycled so that the processor ignores frames illuminated for security purposes.

A typical security camera may take 25 images or frames per second. Smoke detection may only require detecting 1 frame per second or less. Therefore the remaining 30 images can be used for security purposes.

To give increased sensitivity, video processing software operating within the detection sub-system (6,7) may be used to eliminate the contribution of nuisance changes in video signals which are not in the location known to be occupied by the light beam. Software based systems which perform a similar function of processing distinct areas of a video image are known, for example in video-based security systems such as Vision System's ADPRO™ products.

The emitter may be a laser, emitting polarised radiation. The laser may emit visible radiation, infrared radiation or ultra violet radiation. Selection of the wavelength of the radiation may be dependent on the characteristics of the particles to be detected, as well as the characteristics of the apparatus and method to be employed in the detection of the particles. Other types of radiation emitter may comprise a xenon flash tube, other gas discharge tubes, or a laser diode or light emitting diode. The light is preferably collimated to at least some degree, but if the optional area segregation using regions of interest is employed, a broader radiation beam may be emitted.

Figure 11C:
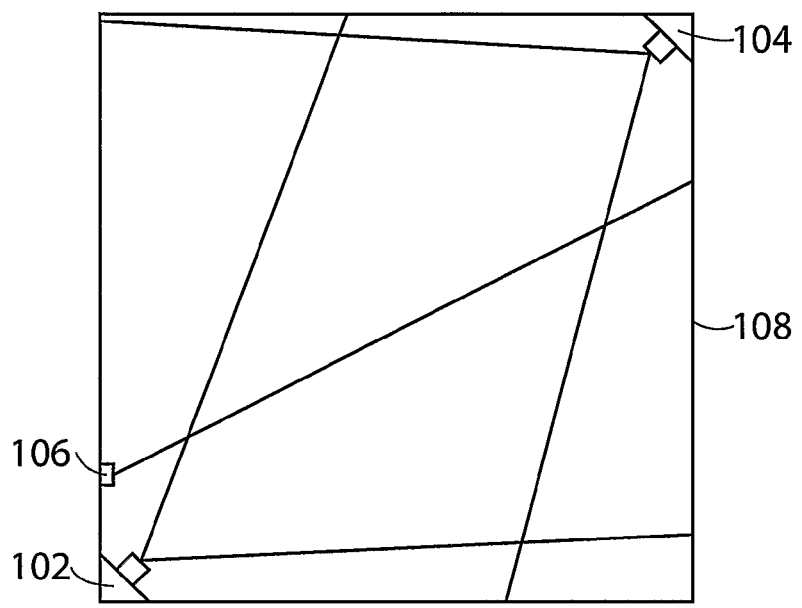

A further embodiment is shown in FIG. 11c, which employs two cameras 102 and 104, and a single laser 106. In this embodiment, one camera can view the emitter, and the other the position or target where the radiation hits the wall 108. In such a configuration, it is desirable if the cameras 102, 104 are connected to the same processor or at least communicate with each other. This system provides many advantages, such as confirmation that the radiation is not blocked, and can be used to determine more accurately a position of the emitter radiation with respect to camera 104, which detects the forward scatter of light. As such, the degree of uncertainty of the position of the path of the emitted radiation is reduced, and the regions of interest can be reduced in size, increasing the sensitivity of the detector system. Further, as it is known that large particles, commonly caused by fire, forward scatter more than smaller particles (often associated with dust), a determination of particle characteristics can be made. If there is significantly more forward scatter than back scatter for a particular segment of the emitted radiation path, then it may be interpreted that the particle density at that particular segment consists of a proportion of large particles. It may be useful to compare this to other segments or other times, in order to ascertain characteristics of the event that caused the particles to be present in the first place.

While this invention has been described in connection with specific embodiments thereof, it will be understood that it is capable of further modification(s). This application is intended to cover any variations uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof.

What is claimed is:

1. A method of detecting particles comprising the steps of:
    emitting a beam of radiation, wherein the beam has a path within a field of view of an image capturing device;
    capturing images with the image capturing device, wherein an area in the images contains the path of a beam of radiation;
    determining an integration region in the images, being the area in the images containing the path;
    determining background regions in the images, being the areas on either side of the integration region;
    compensating for variation in illumination levels in the integration region based on illumination levels in the background regions; and
    detecting a variation in the images indicating an increase in scattered radiation in the integration region due to the presence of particles.

2. The method as claimed in claim 1 wherein the emitted beam is modulated and the method further includes:
    capturing a plurality of images including, "on" frames, being images when the modulated beam of radiation is emitted, and "off" frames, being images when the modulated beam of radiation is not emitted.

3. A method as claimed in claim 2 wherein background cancellation includes subtracting off frames from on frames.

4. A method as claimed in claim 1 wherein the method includes sub-dividing the integration region and background regions along the path of the beam of radiation and determining a brightness compensation factor for each subdivision.

5. A method as claimed in claim 2 wherein the brightness compensation factor f is defined as:

$$f = \frac{\left(\frac{\mu_{on1}}{\mu_{off1}} + \frac{\mu_{on2}}{\mu_{off2}}\right)}{2}$$

where $\mu_{on1}$ is the average value of pixel intensity in background region 1, in the "on" frame; $\mu_{off1}$ is the average value of pixel intensity in background region 1, in the "off" frame; $\mu_{on2}$ is the average value of pixel intensity in background region 2, in the "on" frame; and $\mu_{off2}$ is the average value of pixel intensity in background region 2, in the "off" frame.

6. A method as claimed in claim 2 wherein the method includes scaling the off frames by the brightness compensation factor to compensate for variance in illumination of the images.

7. A method as claimed in claim 1 which includes summing, averaging or low-pass filtering a plurality of background cancelled frames to reduce noise.

8. A method as claimed in claim 1 wherein the image comprises pixels wherein the method includes:
    determining a system geometry, wherein each pixel corresponds to a specific geometric configuration with respect to a scattering volume, wherein at each pixel, the following parameters can be determined:
    θ—scattering angle;
    r—the distance in meters from the scattering volume to a laser source that emits the beam;
    D—distance from image capturing device to the laser source; and
    L—physical length viewed by one pixel at a given point along the beam path; and
    correcting an intensity of each pixel within the integration region to correct for variation due to at least one of system geometry or scattering angle.

9. A method as claimed in claim 1, wherein the beam is divided into a number of sectors corresponding to respective physical lengths of the beam, wherein obscuration for a particular sector is the sum of all the pixel intensities which fall into the physical length and position described by that sector, wherein the method includes: integrating over the sectors to obtain the detected obscuration by particles.

10. A method as claimed in claim 1 wherein the image capturing device is a camera and the beam is a laser beam.

11. A method as claimed in claim 1 wherein the increase in scattered radiation is assessed with reference to a threshold value, wherein the method comprises assigning different threshold values for different spatial positions along the beam.

12. A method according to claim 1, wherein the integration region is generally triangular, wherein the integration region is wider further away from the laser source.

13. A method according to claim 1, wherein the integration region is defined to be a narrow area to reduce the noise contributions from pixels that are not contributing a scattering signal.

14. A method according to claim 1, wherein the integration region and the background regions are updated periodically to reflect any detected changes in a location of a source of the emitted beam.

15. Apparatus adapted to detect particles, said apparatus comprising a source of a beam of radiation, at least one image capturing device, and a processor means adapted to operate in accordance with a predetermined instruction set, said apparatus, in conjunction with said instruction set, being adapted to perform the method as claimed in claim 1.

16. A method of detecting particles comprising the steps of:
    emitting a beam of radiation, wherein the beam has a path within a field of view of an image capturing device;
    capturing images with the image capturing device, wherein an area in the images contains the path of a beam of radiation;
    compensating illumination levels in the images, based on illumination levels in the images outside of said area; and detecting a variation in the images indicating an increase in scattered radiation from the beam due to the presence of particles.

17. A method according to claim 16, wherein the emitted beam is modulated and the method includes:
   capturing a plurality of images including, "on" frames, being images when the modulated beam of radiation is emitted, and "off" frames, being images when the modulated beam of radiation is not emitted; and
   subtracting "emitter off" frames from "emitter on" frames, wherein background cancellation includes scaling "emitter off" frames by the brightness compensation factor.

18. A method according to claim 16, wherein the method includes wherein the illumination levels in the images outside of said area are determined from background regions in the image on opposite sides of the area that contains the path of a beam.

19. A method according to claim 17, wherein the method includes determining two background regions for interpolation of a brightness compensation factor for correcting temporal variations in background lighting on either side of the path of the beam, in the laser off images.

20. A method according to claim 19, wherein the interpolating the brightness compensation factor includes:
   determining an average of a first ratio and a second ratio, wherein:
   the first ratio is the average value of pixel intensity in a first of the background regions when the modulated beam of radiation is emitted, compared to the average value of pixel intensity in the first of the background regions when the modulated beam of radiation is not emitted; and
   the first second ratio is the average value of pixel intensity in a second of the background regions when the modulated beam of radiation is emitted, compared to the average value of pixel intensity in the second of the background regions when the modulated beam of radiation is not emitted.

* * * * *